United States Patent
Karladani (10) Patent No.: US 11,266,683 B2
(45) Date of Patent: Mar. 8, 2022

(54) ANTIMICROBIAL AND CLEANSING COMPOSITION CONSISTING OF A POLYMERIC BIGUANIDE AND EDTA

(71) Applicant: SUNMEDIC AB, Limhamn (SE)

(72) Inventor: Abbas Karladani, Limhamn (SE)

(73) Assignee: Sunmedic AB, Linhamn (SE)

( * ) Notice: Subject to any disclaimer, the term of this patent is extended or adjusted under 35 U.S.C. 154(b) by 28 days.

(21) Appl. No.: 16/076,072

(22) PCT Filed: Feb. 8, 2017

(86) PCT No.: PCT/EP2017/052713
§ 371 (c)(1),
(2) Date: Aug. 7, 2018

(87) PCT Pub. No.: WO2017/137419
PCT Pub. Date: Aug. 17, 2017

(65) Prior Publication Data
US 2021/0015851 A1   Jan. 21, 2021

(30) Foreign Application Priority Data
Feb. 9, 2016   (SE) ................... 1650162-9

(51) Int. Cl.
| A61K 31/785 | (2006.01) |
| A61P 17/02 | (2006.01) |
| A61K 31/14 | (2006.01) |
| A61K 31/197 | (2006.01) |
| A61K 47/10 | (2017.01) |
| A61K 47/18 | (2017.01) |
| A61K 47/26 | (2006.01) |

(52) U.S. Cl.
CPC ............ *A61K 31/785* (2013.01); *A61K 31/14* (2013.01); *A61K 31/197* (2013.01); *A61K 47/10* (2013.01); *A61K 47/183* (2013.01); *A61K 47/26* (2013.01); *A61P 17/02* (2018.01)

(58) Field of Classification Search
CPC ..................................................... A61P 17/02
See application file for complete search history.

(56) References Cited

U.S. PATENT DOCUMENTS

| 6,303,557 B1* | 10/2001 | Colclough ............... C11D 3/48 510/382 |
| 2002/0022660 A1 | 2/2002 | Jampani et al. |
| 2009/0069436 A1 | 3/2009 | MacGregor |
| 2009/0170947 A1 | 7/2009 | Aggarwal et al. |
| 2009/0214628 A1* | 8/2009 | de Rijk .................. A61K 9/127 424/450 |
| 2010/0036334 A1 | 2/2010 | Heagle et al. |
| 2012/0107415 A1 | 5/2012 | Lisowsky et al. |
| 2013/0150451 A1* | 6/2013 | Salamone ............... A01N 37/52 514/635 |

FOREIGN PATENT DOCUMENTS

| CN | 101437394 A | 5/2009 |
| CN | 102883708 A | 1/2013 |
| CN | 103153290 A | 6/2013 |
| EP | 1404311 A1 | 4/2004 |
| EP | 2896395 A1 | 7/2015 |
| WO | 2001035743 A1 | 5/2001 |
| WO | 2005097094 A1 | 10/2005 |
| WO | 2007068938 A2 | 6/2007 |
| WO | 2012080918 A2 | 6/2012 |
| WO | 2013086181 A1 | 6/2013 |

OTHER PUBLICATIONS

Convergent Cosmetics, scientificspectator, last modified date: Jul. 28, 2015 acquired from the source code of the webpage http://www.scientificspectator.com/documents/personal%20care%20spectator/HLB_Basics.pdf (Year: 2015).*
Acton, Claire, Medihoney: a complete wound bed preparation product. Br J Nurs. 2-25;17(11):S44-S468, 2008.
Simon Finnegan and Steven L. Percival, "EDTA: An Antimicrobial and Antibiofilm Agent for Use in Wound Care", Advances in Wound Care, vol. 4, No. 7, 415-421, 2015.
Georgina Gethin, The significance of surface pH in chronic wounds, Wounds 3:52-56, 2007.
Tony J. Hall et al., A comparison of the antibacterial efficacy and cytotoxicity to cultured human skin cells of 7 commercial hand rubs and Xgel, a new copper-based biocidal hand rub, Am J Infect Control, 37(4):322-6, 2009.
Handler, SIAM, 22, 18-21. Apr. 2006.
A.B. Jull et al, Honey as a topical treatment for wounds. Cochrane Database Syst Rev 6(3):CD005083, 2015 (book + summary).

(Continued)

*Primary Examiner* — Mark V Stevens
*Assistant Examiner* — Alparslan Asan
(74) *Attorney, Agent, or Firm* — Dinsmore & Shohl LLP; Weston R. Gould (57) ABSTRACT

The invention relates to a antimicrobial and cleansing composition consisting of a. a polymeric biguanide, and b. a metal ion chelating agent, and g. a solvent, wherein the ratio of a:b is between 0.75:2.25 and 1.25:2.25, or about 1:2, and optionally one or more of the following ingredients; c. a quaternary ammonium salt, d. at least one surfactant, e. a humectant and f. a gelling agent. The invention further relates to said composition for use in a treatment, prevention or reduction of a disease, disorder or condition related to microbials, or treatment, prevention or reduction of infection, or inflammation, or infected wounds, or inflamed wounds, or treatment, prevention or reduction of biofilms, or removal of necrotic tissue. A liquid flow system may be used for administration of the composition.

16 Claims, 1 Drawing Sheet

(56) References Cited

OTHER PUBLICATIONS

Yi-Ching Li et al., Assessment of the cytotoxicity of chlorhexidine by employing an in vitro mammalian test system, Journal of Dental Sciences 9, 130-135, 2014.

Petra Ševcíková et al., Formulation, antibacterial activity, and cytotoxicity of 1-monoacylglycerol microemulsions Eur. J. Lipid Sci. Technol. 116, 448-457, 2014.

Andrzej Starek and Wieslaw Szymczak., Hematological effects of four ethylene glycol monoalkyl ethers in short-term repeated exposure in rats, Arch Toxicol, 82:125-136, 2008.

* cited by examiner

ANTIMICROBIAL AND CLEANSING COMPOSITION CONSISTING OF A POLYMERIC BIGUANIDE AND EDTA

TECHNICAL FIELD

The present invention is directed toward an antimicrobial, cleansing composition and use thereof, in particular for therapeutic use in biofilms, soft-tissue wounds, infected cavities, and infected bones.

BACKGROUND OF THE INVENTION

Infected Wound

Infections occur in a minor but significant portion of the patients undergoing joint replacement surgery or fracture fixation, particularly those with open fractures. Once established, infections are difficult to eradicate, especially in the case of bacterial biofilm formation on implanted hardware. Wounds are a significant source of cost to patients as well as to health care system, specially wound that are complicated with infection.

Biofilm formation on orthopaedic implants is attributed to the glycocalyx-mediated surface mode of bacterial growth and is usually treated through a secondary surgery involving irrigation, debridement and the appropriate use of antibiotics, or complete removal of the infected implant.

When a wound is colonized with microorganisms they survive as polymicrobial communities encased within a matrix of extracellular polymeric substance (EPS). This community of microorganisms are attached to each other, often in conjunction with a surface, and form community of microorganisms. The combination of a community of microorganisms, encased within self-generated EPS and attached onto a surface (liquid or solid) is simply defined as a biofilm. In heavily contaminated, infected or chronic wounds with bacteria colonization and biofilm, the debridement is the first step to facilitating successful wound closure. Wound debridement of infected tissues may help control infection and bioburden.

Research has shown that the lowest concentration required to kill or eliminate bacterial biofilm for many antibiotics actually exceeds the maximum prescription levels for the antibiotics. The widespread use of antibiotics has resulted in the development of numerous microbial resistances. The continuing rise of bacterial resistance to antibiotics is a serious concern. Therefore, there is an unmet need to develop and include parallel approaches that target infections, especially those complicated by the presence of biofilms.

In general, biocides have a broader spectrum of activity than antibiotics. Antibiotics tend to have specific intracellular targets, while biocides or antiseptics or antimicrobials (which terms are interchangeable in this specification) may have multiple targets.

Antiseptics are effective through many mechanisms of action. This makes the development of resistance to them unlikely, in contrast to antibiotics.

Maintenance debridement and use of topical antimicrobials (antiseptics) are believed to be more effective than antibiotic therapy.

In recent years, topical antimicrobial agents have become the first line of treatment in managing bacterial burden, particularly in chronic wounds. The use of many antiseptics in wound management must be subject to a risk-benefit assessment of possible local toxicity and beneficial antibacterial action. In short, it is advised that, before use, the beneficial antimicrobial effects and bioavailability should be weighed against any possible cellular toxicity. A variety of antimicrobial compositions, articles and methods have been suggested. However, such wound compositions and methods possess various deficiencies and shortcomings, and therefore also prevent long term use of the composition.

EP1404311 discloses a composition for use as a wound treatment agent which is suitable as a washing or shower gel for decontaminating surfaces of the body, for dissolving incrustations or scabs from body surfaces or as a dissolving gel for dressings and for changing moist dressing. Disclosed is a use of a surfactant and biguanide hydrochloride, and use of amphoteric or non-ionic surfactants in combination with biguanide hydrochloride (PHMB). Furthermore, the preferred surfactant for this formulation is a betaine and, in particular, an amidoalkyl betaine of a fatty acid. However, said formulation does not contain any compound, which might enhance biocidal effect of PHMB. On the contrary, said surfactants might reduce the biocidal effect of PHMB, which may have negative effects on the further treatment of wounds.

EP2896395 discloses a liquid or a gel containing polyhexamethylene biguanide (PHMB) and a non-ionic surfactant and at least one co-surfactant with or without substances obtained from herbs, for topical wound treatment. The preferred non-ionic surfactant are tri-block co-polymers of polyethylene oxide and polypropylene oxide. The tri-block copolymer is preferably a poloxamer, particularly poloxamer 188. Poloxamers generally are believed to be ineffective in wound healing, but effective in reducing postsurgical adhesions in several test systems. Furthermore, there is no mention of the use of a chelating/sequestrant agent in combination with biguanide hydrochloride.

US2012/0107415 discloses a combined disinfection and decontamination agent comprising at least one vitamin, at least one metal ion, at least one active-surface compound, and at least one further antimicrobial active substance. The antimicrobial active substance is an alcoholic active substance.

US2009/0069436 discloses an antimicrobial hand wash (skin) composition comprising biguanide or a quaternary compound. Also disclosed is a composition for skin rub, in which case it may additionally comprise at least one alcohol, at least one lipogel and at least one oil. Alternatively, the composition may be a skin wash, in which case it may additionally comprise at least one detergent agent and at least one amphoteric surfactant.

US2002/0022660 discloses use of at least one alcohol (30-65 percent by weight) and biguanide and a combination of a surfactant as a deep penetrating antimicrobial compositions for the skin as outlined below. The use of alcohols is preferably avoided, due to its known high cellular toxicity.

WO2007068938 discloses an antimicrobial composition suitable for use on skin and wounds comprising a source of an antimicrobial agent and an agent, which disrupts biofilms. Disclosed is a use of EDTA as the agent that disrupts biofilms and the antimicrobial agent is selected from the group of iodine, ionic silver or an oxidizing agent, such as sodium hypochlorite or chlorine dioxide. These antimicrobial agents have shown to have higher cellular toxicity.

WO2013086181 discloses a combination of at least one antimicrobial polymeric biguanide and at least one antimicrobial vicinal diol to diminish or eliminate biofilm communities. Described is a method of treating a surface, or a surgical dressing, and in dentistry, such as for gingivitis. Since the antimicrobial monoalkyl vicinal diols in this invention have low or negligible water solubility, adding a surfactant is necessary. Suitable surfactants disclosed are cationic, anionic, non-ionic, amphoteric and ampholytic surfactants. However, these surfactants are used in high doses, particularly anionic surfactants in numerous forms and different applications, which results in a need of larger amounts of antimicrobial agent, such as polymeric biguanide to maintain the composition's biocidal effect. This raises concern regarding cellular toxicity of the composition. The cellular toxicity of the said composition has not been studied.

EP 1139759 discloses a disinfectant and cleaner solution that is formulated to apply on hard surface. The composition comprises a polymer biguanide, a quaternary ammonium salt, a sequestrant, and a cleaning agent. It does not disclose a use of the composition in wound treatment or on a vital surface. Therefore, the cellular toxicity of the composition is not tested.

A common treatment in both dentistry and the food/water industry is the use of anti-biofilm agents, such as EDTA for controlling biofilms. EDTA compositions are highly effective in eliminating existing biofilms, and preventing biofilm formation. At low concentrations EDTA has been shown to prevent biofilms by inhibiting the adhesion of bacteria. Furthermore, it has also been shown to reduce biofilm colonization and proliferation.

Biguanide compound composed of a synthetic mixture of polymers. The antiseptic agent polyhexamethylene biguanide (also known as polihexanide or PHMB) has been used for over 60 years in a wide range of applications from swimming pool sanitizers to preservatives in cosmetics and contact lens solutions. In recent years, PHMB has been used as a wound irrigation fluid. PHMB has an effect on both planktonic bacteria and those in biofilms. It has been shown that PHMB is safe for clinical use. In the standard comparative tests of 12 the biocompatibility tests against other commonly used therapies PHMB has demonstrated its superiority to chlorhexidine, povidone-iodine, triclosan, silver and sulphadiazine. In addition, no known resistance to PHMB has been reported, most likely owing to its rapid and non-specific bactericidal activity.

Ingredients commonly used in antibacterial composition, such as chlorhexidine, alcohols and glycols have undesired side effects. Especially for long term treatment, i.e. more than two days, these ingredients may cause side effects, such as cell toxicity.

US2013/0150451 discloses a composition comprising a biguande and a vicinal diol (a monoalkyl glycol, monoalkyl glycerol or a monoacyl glycerol). The composition may further comprise a chelating agent, a surfactant, etc.

Handler, SIAM 22, 18-21, April 2016, page 3, line 4-7, "Hydrophobic long chain alcohol", discusses the toxicity of alcohol, such as vicinal diols. Hall et. al, www.ajicjournal.org, Vol 37 No 4, page 326, left column, line 40-47, discloses other undesirable effect of alcohol-based hand rubs including absorption into the blood and the removal of lipid considered essential for the integrity of the skin. See also Sevcikova Petra, et. Al., European J. of Lipid Science and Technology, April 2014, page 448, line 35-36 and 455, left column, line 21-28 showing that 1-monoacylglycerol has a dose dependent cytotoxicity from mild to severe.

Yi-Ching Li et. al, J. Dental Science (2014), 9, 130-135, discloses on page 133 that chlorhexidine induces apoptosis at lower concentration and causes necrosis at higher concentration on fibroblasts.

Animal and human studies have shown that Ethylene glycol alkyl ethers (EGAEs) can cause adverse reproductive, developmental, and hematological effects through inhalation, dermal absorption, and ingestion (Andrzej Starek et. al, Arch Toxicol (2008) 82:125-136, especially on page 126, line 8-11. On page 127, right column, line 20-21 they demonstrated also hematological changes in the peripheral blood in their material that were produced by all of four tested EGAEs.

SUMMARY OF THE INVENTION

The present invention relates to antimicrobial and cleansing compositions, whereby the composition has minimal or no cellular toxicity for mammal cells. The new composition is especially useful for long term treatment of wounds, i.e. treatment for a period of more than two days, five days, a week or two weeks. The new composition reduces costs for health care.

The present invention relates to a composition consisting of
a. a polymeric biguanide,
b. ion chelating agent, and
g. a solvent
whereby the composition in addition optionally may consist of one or more of the following ingredients
c. a quaternary ammonium salt,
d. at least one surfactant,
e. a humectant, and
f. a gelling agent.

In one embodiment, the composition does not consist an anionic surfactant or an alcohol. In another embodiment, the composition has a pH between 4 and 8. A buffer may be used in the composition. In a further embodiment, the solvent is water.

The polymeric biguanide may be polyhexamethylene biguanide.

The ion chelating agent may be ethylenediaminetetraacetic acid (EDTA), as a disodium, trisodium, tetrasodium salt or mixtures thereof. In one embodiment, the ion chelating agent is disodium EDTA. In another embodiment, the ion chelating agent is trisodium EDTA. In a further embodiment, the ion chelating agent is tetrasodium EDTA. In one embodiment, the ion chelating agent is a combination of disodium ethylenediaminetetraacetic acid salt and trisodium ethylenediaminetetraacetic acid salt.

The present composition regards a non-alcoholic antimicrobial composition, which is an effective antimicrobial, cleansing products with no or negligible cellular toxicity. The present innovation provides an antimicrobial, cleansing composition which combines known and effective biocide agents in low dose. It is believed that due to synergistic interaction, said composition exhibits a total antimicrobial effect that is greater than the sum of effects from all individual antimicrobial agents. The result from an experimental animal study, show that said compositions with multiple low dose biocides agents result in effective antimicrobial, cleansing products with no or negligible cellular toxicity and comparable with medical honey. The new composition is especially useful for long term treatment, over a period of one, two or three weeks, of a wound that may be infected or inflamed.

In one embodiment, the composition consists of
a. a polymeric biguanide, and
b. a metal ion chelating agent, and
g. a solvent,
wherein the ratio of a:b is between 0.75:2.25 and 1.25:2.25, or about 1:2.

In another embodiment, the composition consists of
a. a polymeric biguanide in an amount of 750 to 1250 ppm, or about 1000 ppm,
b. ion chelating agent in an amount of 1750 to 2250 ppm, or about 2000 ppm, and
g. a solvent up to 100 wt %%, and optionally
e. a humectant in an amount of 40000 to 100000 ppm, or about 50000 or 85000 ppm.

The composition of the present invention is believed to provide a synergistic interaction between a polymeric biguanide and a metal ion chelating agent to further enhance its antibacterial, cleansing effect and removal of the slough and necrotic tissue from a wound.

In one embodiment, the composition consists of
a. a polymeric biguanide,
b. a metal ion chelating agent,
c. a quaternary ammonium salt, and
g. a solvent
wherein the ratio of a:b:c is between 0.75:2.25:0.30 and 1.25:2.25:1.25, or about 1:2:1.

In another embodiment, the composition consists of
a. a polymeric biguanide in an amount of 750 to 1250 ppm, or about 1000 ppm,
b. ion chelating agent in an amount of 1750 to 2250 ppm, or about 2000 ppm,
c. a quaternary ammonium salt in an amount of 400 to 1250 ppm, or about 500 or 1000 ppm, and
g. a solvent up to 100 wt %%, and optionally
e. a humectant in an amount of 40000 to 100000 ppm, or about 50000 or 85000 ppm.

The composition of the present invention is believed to provide additional synergistic interaction between a polymeric biguanide, and a metal ion chelating agent through the addition of a quaternary ammonium salt to further enhance its antibacterial, cleansing effect and removal of the slough and necrotic tissue from a wound. This allows for use of the ingredients in low doses with improved healing, even for long term treatment and without toxic effects on the cells of the tissue to be treated.

In one embodiment, the composition consists of
a. a polymeric biguanide,
b. a metal ion chelating agent,
d. at least one surfactant, and
g. a solvent
wherein the ratio of a:b:d is between 0.75:2.25:0.75 and 1.25:2.25:2.25, or about 1:2:2.

In another embodiment, the composition consists of
a. a polymeric biguanide in an amount of 750 to 1250 ppm, or about 1000 ppm,
b. ion chelating agent in an amount of 1750 to 2250 ppm, or about 2000 ppm,
d. at least one surfactant in an amount of 1750 to 2250 ppm, or about 2000 ppm, and
g. a solvent up to 100 wt %, and optionally
e. a humectant in an amount of 40000 to 100000 ppm, or about 50000 or 85000 ppm.

In a further embodiment, the composition consist of
a. polyhexamethylene biguanide, in an amount of 750 to 1250 ppm, or about 1000 ppm,
b. EDTA in an amount of 1750 to 2250 ppm, or about 2000 ppm,
d1 polysorbate 60 in an amount of 750 to 1250 ppm, or about 1000 ppm,
d2. undecylenamidopropyl betaine in an amount of 750 to 1250 ppm, or about 1000 ppm,
g. water up to 100 wt %, and
e. glycerin in an amount of 40000 to 100000 ppm, or about 50000 or 85000 ppm.

The composition of the present invention is believed to provide additional synergistic interaction between a polymeric biguanide, and a metal ion chelating agent through the addition of at least one surfactant to further enhance its antibacterial, cleansing effect and removal of the slough and necrotic tissue from a wound. This allows for use of the ingredients in low doses with improved healing, even for long term treatment and without toxic effects on the cells of the tissue to be treated.

In one embodiment, the composition consists of
a. a polymeric biguanide,
b. a metal ion chelating agent,
c. a quaternary ammonium salt,
d. at least one surfactant; and
g. a solvent
wherein the ratio of a:b:c:d is between 0.75:2.25:0.30:0.75 and 1.25:2.25:1.25:2.25, or about 1:2:1:2.

In another embodiment, the composition consists of
a. a polymeric biguanide in an amount of 750 to 1250 ppm, or about 1000 ppm,
b. ion chelating agent in an amount of 1750 to 2250 ppm, or about 2000 ppm,
c. a quaternary ammonium salt in an amount of 400 to 1250 ppm, or about 500 or 1000 ppm,
d. at least one surfactant in an amount of 1750 to 2250 ppm, or about 2000 ppm, and
g. a solvent up to 100 wt %, and optionally
e. a humectant in an amount of 40000 to 100000 ppm, or about 50000 or 85000 ppm.

In a further embodiment, the composition consist of
a. polyhexamethylene biguanide in an amount of 750 to 1250 ppm, or about 1000 ppm,
b. EDTA in an amount of 1750 to 2250 ppm, or about 2000 ppm,
c. benzalkonium chloride in an amount of 750 to 1250 ppm, or about 1000 ppm,
d1 polysorbate 60 in an amount of 750 to 1250 ppm, or about 1000 ppm,
d2. undecylenamidopropyl betaine in an amount of 750 to 1250 ppm, or about 1000 ppm,
g. water up to 100 wt %, and
e. glycerin in an amount of 40000 to 100000 ppm, or about 50000 or 85000 ppm.

The composition of the present invention is believed to provide additional synergistic interaction between a polymeric biguanide, a metal ion chelating agent and a quaternary ammonium salt through adding at least one non-ionic surfactant to further enhance its antibacterial, cleansing effect and removal of the slough and necrotic tissue from a wound.

The composition of the present invention is believed to provide additional synergistic interaction between a polymeric biguanide, a metal ion chelating agent and a quaternary ammonium salt through adding at least one amphoteric surfactant to further enhance its antibacterial, cleansing effect and removal of the slough and necrotic tissue from a wound.

In another embodiment, the at least one surfactant includes at least one non-ionic surfactant or at least one amphoteric surfactant or mixtures thereof, which surfactants have a hydrophilic-lipophilic balance value between 8 and 20, or between 10 and 18. In one embodiment, the non-ionic surfactant may be Polysorbate or Polysorbate 60.

In a further embodiment, the amphoteric surfactant may be undecylenamidopropyl betaine or cocobetaine.

In a further embodiment, the composition consists of
a. a polymeric biguanide in an amount of 750 to 1250 ppm, or about 1000 ppm,
b. ion chelating agent in an amount of 1750 to 2250 ppm, or about 2000 ppm, and
g. a solvent up to 100 wt %,
and optionally one or more of the following ingredients
c. a quaternary ammonium salt in an amount of 400 to 1250 ppm, or about 500 or 1000 ppm,
d. at least one surfactant in an amount of 1750 to 2250 ppm, or about 2000 ppm,
e. a humectant in an amount of 40000 to 100000 ppm, or about 50000 or 85000 ppm, and
f. a gelling agent in an amount of 1.5 to 2.5 wt %, or about 1.8 wt %, In yet a further embodiment, the composition consists of
a. a polymeric biguanide in an amount of 750 to 1250 ppm, or about 1000 ppm,
b. ion chelating agent in an amount of 1750 to 2250 ppm, or about 2000 ppm,
d. at least one surfactant in an amount of 1750 to 2250 ppm, or about 2000 ppm,
e. a humectant in an amount of 40000 to 100000 ppm, or about 50000 or 85000 ppm, and
g. a solvent up to 100 wt %, and optionally one or more of the following ingredients
c. a quaternary ammonium salt in an amount of 400 to 1250 ppm, or about 500 or 1000 ppm, and
f. a gelling agent in an amount of 1750 to 2250 ppm, or about 2000 ppm, The polymeric biguanide as used in any of the compositions outlined above may be polyhexamethylene biguanide (PHMB).

The ion chelating agent as used in any of the compositions outlined above may be ethylenediaminetetraacetic acid (EDTA).

The quaternary ammonium salt as used in any of the compositions outlined above may be benzalkonium chloride.

The at least one surfactant as used in any of the compositions outlined above may be Polysorbate or Polysorbate 60, or undecylenamidopropyl betaine or cocobetaine.

The humectant as used in any of the compositions outlined above may be glycerine.

The gelling agent as used in any of the compositions outlined above may be hydroxyethyl cellulose.

The solvent as used in any of the compositions outlined above may be water.

The pH in any of the compositions outlined above may be between 4 and 8, or 5 and 7, or 5.5 and 6.5.

The hydrophilic-lipophilic balance value in any of the compositions outlined above may be between 8 and 20 or between 10 and 18.

In an embodiment, the composition consists of
a. polyhexamethylene biguanide in an amount of 750 to 1250 ppm, or about 1000 ppm,
b. ethylenediaminetetraacetic acid in an amount of 1750 to 2250 ppm, or about 2000 ppm,
d1. one surfactant selected from Polysorbate or Polysorbate 60, in an amount of 750 to 1250 ppm, or about 1000 ppm,
d2. one surfactant selected from undecylenamidopropyl betaine or cocobetaine, in an amount of 750 to 1250 ppm, or about 1000 ppm,
e. glycerine in an amount of 40000 to 100000 ppm, or about 50000 or 85000 ppm, and
g. water up to 100 wt %, and optionally
f. hydroxyethyl cellulose in an amount of 1.5 to 2.5 wt %, or about 1.8 wt %, and
c. benzalkonium chloride in an amount of 400 to 1250 ppm, or about 500 or 1000 ppm, wherein the pH of the composition is between 4 and 8, or 5 and 7, or 5.5 and 6.5.

The antimicrobial, cleansing composition according to the present invention pertains to eliminate microorganisms including, but not limited to, gram negative and gram positive bacteria, virus, yeast, fungi, protozoa in wounds. The antimicrobial, cleansing composition according to the present invention is a polymeric biguanide base composition that shows similar negligible or no cellular toxicity as medical honey. The composition has no bacterial resistance and can thus be used with improves efficacy against multi-drug-resistant organisms, which may infect wounds and lead to increased morbidity, including the methicillin-resistant *Staphylococcus aureus* and *Pseudomonas aeruginosa*. The composition accelerates wound healing, especially during long term treatment due to the negligible cell toxicity of the composition.

The new composition can be used for wound healing in a mammal, such as a human, especially for removal of a biofilm. The wounds may be present inside the mammal body or be present on the skin of the mammal. Low doses of the ingredients as present in the composition allow the use of the composition with minimal or no cellular toxicity for the mammal cells. This improves wound healing. The new composition thus improves safety, efficacy and efficiency of wound healing compared to known compositions.

Due to the negligible or low cell toxicity of the composition, the composition is useful for long term treatment of a wound, such as treatment for more than two or five or ten or fourteen or twenty one, or more days.

The antimicrobial, cleansing composition according to the present invention pertains for treatment of wounds containing soft-tissue and/or bones. The composition can be used as wound irrigation solutions either manually or automatically using Negative Pressure Wound Therapy devices. The composition can be made in form of ointments, creams, gels, solutions and wound dressings.

The composition of the invention may be a pharmaceutical composition.

The inventions relates to the composition as defined herein for use as a medicament. The composition as defined herein, can be used in the treatment, prevention or reduction of a disease, disorder or condition related to microbials, with reduced or without cellular toxicity for the cells. The composition as defined herein, can be used in the treatment, prevention or reduction of infected or inflamed wounds in a mammal. The infection or inflammation may be a cure or chronic. The mammal may be a human or an animal, such as a rat. The composition as defined herein, can be used for debridement of wounds and for removal of necrotic tissue. The inventions relates to the composition as defined herein for use in a treatment, prevention or reduction of a disease, disorder or condition selected from the group comprising or consisting of acute or chronic infection, acute or chronic inflammation, such as gingivitis, diabetic ulcers, second-degree partial-thickness burns, traumatic wounds, *Acanthamoeba keratitis*, etc.

The invention relates to a use of the composition as defined herein in a treatment, prevention or reduction of a disease, disorder or condition related to microbials. The invention relates also to a use of the composition as defined herein for the treatment, prevention or reduction of growth of microbials, especially in wounds present in or on a mammal. The invention especially relates to a use of the composition as defined herein for a treatment or prevention of biofilms or the reduction of formation of biofilms, such as biofilms in the middle ear. Said biofilms being produced by the microbials. The invention further relates to a use of the composition as defined herein for debridement of wounds and for removal of necrotic tissue and/or improvement of wound healing. Further, the invention relates to a use of the composition as defined herein for a treatment, prevention or reduction of infected bones and/or infected cavities in a mammal body.

The invention also relates to topical administration of the composition as defined herein for use in a treatment, prevention or reduction of a disease, disorder or condition related to microbials, or treatment, prevention or reduction of a disease, disorder or condition selected from the group comprising or consisting of acute or chronic infection, acute or chronic inflammation, such as gingivitis, diabetic ulcers, second-degree partial-thickness burns, traumatic wounds, Acanthamoeba keratitis, necrotizing fasciitis, venous stasis disease, pressure ulcerations, such as leg ulcers, or carcinomas, or treatment, prevention or reduction of acute or chronic infected wounds, or acute or chronic inflamed wounds, or formation of biofilms, or for use in debridement of wounds and for removal of necrotic tissue, in a mammal or any of the uses mentioned above. Said disease, disorder or condition may be a topical infection.

The composition can even be used for disinfection of surfaces, such as bedding, surgery tables, tubing, and reusable medical equipment. The composition can be used for wound cleansing solutions, wound dressings, contact lens solutions, mouth washes solution, cosmetic preservative, food disinfectant, veterinary applications, swimming pool cleaners, and in industrial water treatment.

The composition may be used against *Pseudomonas aeruginosa, Staphylococcus aureus* (also the methicillin-resistant type, MRSA), *Escherichia coli, Candida albicans* (yeast), *Aspergillus brasiliensis* (mold), vancomycin-resistant enterococci, and *Klebsiella pneumoniae* (carbapenenn-resistant enterobacteriaceae).

The invention further relates to a method of treating, preventing or reducing a disease, disorder or condition related to microbials, which comprises administering to a mammal in need thereof a therapeutically effective amount the composition as defined herein. In one embodiment, the method relates to treatment, prevention or reduction of a disease, disorder or condition selected from the group comprising or consisting of acute or chronic infection, acute or chronic inflammation, such as gingivitis, diabetic ulcers, second-degree partial-thickness burns, traumatic wounds, Acanthamoeba keratitis, necrotizing fasciitis, venous stasis disease, pressure ulcerations, such as leg ulcers, or carcinomas, or treatment, prevention or reduction of acute or chronic infected wounds, or acute or chronic inflamed wounds, or formation of biofilms, or for use in debridement of wounds and for removal of necrotic tissue.

The invention also relates to the use of the composition as defined herein, in the manufacture of a medicament for the treatment, prevention or reduction of a disease, disorder or condition related to microbials, or treatment, prevention or reduction of a disease, disorder or condition selected from the group comprising or consisting of acute or chronic infection, acute or chronic inflammation, such as gingivitis, diabetic ulcers, second-degree partial-thickness burns, traumatic wounds, Acanthamoeba keratitis, necrotizing fasciitis, venous stasis disease, pressure ulcerations, such as leg ulcers, or carcinomas, or treatment, prevention or reduction of acute or chronic infected wounds, or acute or chronic inflamed wounds, or formation of biofilms, or for use in debridement of wounds and for removal of necrotic tissue, in a mammal.

The present invention also relates to a system adapted for use in wound healing comprising a negative pressure source, a canister for collecting wound exudate, a reservoir containing the composition as defined above, a liquid injector device for transferring a predetermined volume of the composition and connector tubes to transfer the composition to and from an infected soft tissue or bone, a negative pressure wound dressing, which system is adapted to draw fluid from the reservoir to the wound dressing and draw fluid away from the wound dressing after a holding time of 5 to 60 minutes.

The wound dressing may be soaked with the composition of the invention. Adhesive film or tape may be used to stabilize the wound dressing and tubes.

In one embodiment, the system also comprises a control unit adapted for controlling the flow of composition to and from the wound. In a further embodiment, the control unit is adapted to start the negative pressure source after a holding time of between 5 and 60 minutes, so that the composition is removed from the wound and fresh composition is added to the wound. The system may include valves to further control the flow of composition through the tubes.

The invention also relates to a use of the system as defined above for use in a treatment, prevention or reduction of a disease, disorder or condition related to microbials, or treatment, prevention or reduction of a disease, disorder or condition selected from the group comprising or consisting of acute or chronic infection, acute or chronic inflammation, such as gingivitis, diabetic ulcers, second-degree partial-thickness burns, traumatic wounds, Acanthamoeba keratitis, necrotizing fasciitis, venous stasis disease, pressure ulcerations, such as leg ulcers, or carcinomas, or treatment, prevention or reduction of acute or chronic infected wounds, or acute or chronic inflamed wounds, or formation of biofilms, or for use in debridement of wounds and for removal of necrotic tissue, in a mammal, such as a rat, or any of the uses mentioned above.

An advantage of the system according to the invention is a continuous (periodical) flow of the composition to and from the wound. This prevents biofilm formation, improves efficacy and efficiency of wound healing. The system is especially useful for long term treatment of a wound.

DETAILED DESCRIPTION OF THE INVENTION

Definitions

A wound may be defined as a breakdown in the protective function of the skin, the loss of continuity of epithelium, with or without loss of underlying connective tissue (i.e. muscle, bone, nerves), due to injury to the skin or underlying tissues/organs caused by, but not limited to, a trauma, burns, diabetic ulcers, severe infections, such as necrotizing fasciitis, venous stasis disease, and pressure ulcerations or as a result of disease, such as leg ulcers or carcinomas.

A wound may be defined as a closed cavity with existing pathology as infection, inflammation (open abdominal wound, abscess, infected joint with or without implant), or a cavity which is connected to external environment by a fistula.

Medical honey or (MEDIHONEY® Comvita Ltd, New Zealand) is an advanced wound care dressing used for its clinical ability to promote the removal of necrotic tissue and advance wound healing. Cellular toxicity of the composition of the present invention is compared to Medihoney through an experimental animal study.

"Biofilm" may be defined as colonization with microorganisms as polymicrobial communities encased within a matrix of extracellular polymeric substance (EPS). This community of microorganisms are attached to each other, often in conjunction with a surface, and form community of microorganisms. The combination of a community of microorganisms, encased within self-generated EPS and attached onto a surface (liquid or solid) may be defined as a biofilm.

"A" and "the" are understood to include not just one, but one or more of the subject following the "a" or "the". Thus, a surfactant is understood to means one or more surfactants.

"wt %" is weight percentages of the total weight of the composition.

"ppm" is parts per million.

Microbials may be gram negative and gram positive bacteria, virus, yeast, fungi, protozoa, and the like.

The present invention relates to a wound healing formula comprising at least one antimicrobial polymeric biguanide and at least one metal ion chelating agent, with or without one antimicrobial quaternary ammonium compounds.

Combination of a polymeric biguanide with a metal ion chelating agent and optionally a quaternary ammonium salt may give a synergy effect between these elements at low concentration in order to provide an effective biocides composition. This invention is based not only on providing a composition that shows excellent biocide effect, but also demonstrates a negligible or low cellular toxicity. The combination of active ingredients in low concentration, results in a mixture with low cellular toxicity and better compatibility with the environment.

The term "long term treatment" has the meaning of a treatment for more than two or five or ten or fourteen or twenty one, or more days.

Polymeric Biguanide

A preferred polymeric biguanide is polyhexamethylene biguanide (PHMB) commercially available from e.g. Arch Chemicals (CAS No 51274-09-0).

It is well known that polyhexamethylene biguanide (PHMB) has broad spectrum bactericidal and fungicidal action with good tissue tolerance. PHMB has been used in wound cleansing solutions, wound dressings, contact lens solutions, mouth washes solution, surface disinfectant, cosmetic preservative, food disinfectant, veterinary applications, swimming pool cleaners, and in industrial water treatment.

PHMB has been shown to be effective against *Pseudomonas aeruginosa, Staphylococcus aureus* (also the methicillin-resistant type, MRSA), *Escherichia coli, Candida albicans* (yeast), *Aspergillus brasiliensis* (mold), vancomycin-resistant enterococci, and *Klebsiella pneumoniae* (carbapenenn-resistant enterobacteriaceae).

Tests have been performed on *S. aureus* to investigate the potential risks of this bacterium developing resistance to PHMB. The risk was found to be very low. An additional positive influence on the inflammatory process of wound healing, especially in infected or critically colonized wounds has been the binding of inflammatory parameters such as free radicals, showing its antioxidative potential. The clinical effect of using PHMB in some non-healing wounds has been promising.

Cationic Quaternary Ammonium Compounds

The composition in this invention may comprises a cationic quaternary ammonium compound, which is selected from a group of quaternary ammonium salts with long alkyl chains, such as benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride and domiphen bromide, and mixtures thereof. Preferred used quaternary ammonium compounds are benzethonium chloride, methylbenzethonium chloride, and most preferable is benzalkonium chloride with molecular formula $C_{21}H_{38}ClN$ and CAS No. 8001-54-5.

Quaternary ammonium compounds are cationic detergents, as well as disinfectants and surfactants, and as such can be used to remove organic material. Quaternary ammonium compounds are deactivated by anionic detergents. Certain quaternary ammonium compounds, especially those containing long alkyl chains, are used as antimicrobials and disinfectants.

Quaternary ammonium compounds are believed to act by disrupting the cell membrane and are also good against fungi, amoebas, and enveloped viruses. Quaternary ammonium compounds are lethal to a wide variety of organisms except endospores, *Mycobacterium tuberculosis* and non-enveloped viruses.

Metal Ion Chelating Agents

Suitable chelating agents comprise, but are not limited to, mixed salts of Ethylenediaminetetraacetic acid (EDTA), such as disodium, trisodium, tetrasodium, dipotassium, tripotassium, tetrapotassium, lithium, dilithium, ammonium, diammonium, triammonium, tetraammonium, calcium and calcium disodium, more preferably disodium, trisodium or tetrasodium salts of EDTA, preferably disodium EDTA and tetrasodium EDTA.

EDTA is used in the present invention for its antibiofilm effect. EDTA is a well-known metal chelating agent. EDTA has been used as a permeating and sensitizing agent for treating biofilm-associated conditions in dentistry, on medical devices, and in veterinary and human medicine. The effect of EDTA and its ability to chelate and potentiate the cell walls of bacteria and its ability to destabilize a biofilm by sequestering calcium, magnesium, zinc and iron makes it a suitable agent for use in the prevention and management of biofilms.

EDTA has been utilized for the control of microorganisms and biofilms often by being combined with other actives including alcohol, antibiotics, citric acid, polyhexamethylene biguanide (PHMB), quaternary ammonium compounds, silver, iodine, surfactants and other antiseptics.

Surfactants

The antimicrobial composition in the invention for debridement of wounds, may include at least one non-ionic surfactant or at least one amphoteric surfactant or mixtures thereof. The surfactants can have an HLB (hydrophilic-lipophilic balance) value of 5-25, or 8-20, or 10-18 in order to maintain the biocidal activity of the antimicrobial agents.

The term surfactant comes from the words surface active agent. Surfactants are one of many different compounds that make up a detergent. They are added to remove dirt from skin, clothes and household articles. Surfactants have a hydrophobic part and a hydrophilic part. The hydrophobic part consists of an uncharged carbohydrate group that can be straight, branched, cyclic or aromatic. Dependent on the nature of the hydrophilic part, the surfactants are classified as an-ionic, non-ionic, cationic or amphoteric.

Nonionic Surfactants

A surfactant with a non-charged hydrophilic part, e.g. ethoxylate, is non-ionic. These substances are well suited for cleaning purposes. They have a wide application within cleaning detergents and include groups like fatty alcohol polyglycosides, alcohol ethoxylates etc.

Suitable non-ionic surfactants include Polysorbate 60 with the chemical formula C24H46O6, Registry number CAS 1338-41-6, decyl glucoside, and lauryl glucoside polyethylene glycol esters of fatty acids, e.g., coconut, polysorbate, polyoxyethylene. Other examples may be Polysorbate 20 available under the trademark Tween® 20, polyoxyethylene (40) stearate available under the trademark Myrj® S40, polyoxyethylene (25) propylene glycol stearate available under the trademark Atlas® G 2612, and polyoxyethylene (23) lauryl ether available under the trade-mark Brij® (35).

Other non-ionic surfactants can be added, such as the ethyleneoxide/propylene oxide block copolymers of poloxamers, and poloxamers. Poloxamers and poloxamines are preferred, and poloxamers are most preferred. Poloxamers and poloxamines are available from BASF Corp. under the trademarks of Pluronic® and Tetronic®.

The present invention pertains to the use of polysorbate that have amphiphilic properties and are non-ionic, in particular Polysorbate 60 in combination with PHMB for the treatment of persons and animals suffering from acute or chronic wounds, for example, in wound antiseptics, as wound irrigation solutions manually or as wound irrigation solutions automatically using Negative Pressure Wound Therapy devices, in ointments, creams, gels, solutions and wound dressings.

Amphoteric Surfactants

Amphoteric surfactants for use in the composition in this invention can be selected from a group of betaine, amine oxide and imidazolium derivatives. Of said surfactants, are particularly preferred alkyl betaines, alkyl amine oxides and alkyl imidazolium derivatives.

Preferred alkyl betaines include Lauryldimethylbetaine (Cas No: 683-10-3), Cocobetaine (Cas No: 68424-94-2), Myristyl betaine (Cas No: 2601-33-4), Decyl betaine (Cas No: 2644-45-3), Lauryl sultaine (Cas No: 14933-08-5), Oleyldimethylbetaine (Cas No: 871-37-4), Dodecylbetaine (Cas No: 55142-08-0), Caprylyl betaine (Cas No: 27593-14-2) and Behenyl betaine (Cas No: 26920-62-7).

Preferred amine oxides include Lauramine oxide (Cas No: 1643-20-5), Lauramidopropylamine oxide (Cas No: 61792-31-2), Cocamine oxide (Cas No: 61788-90-7), Cocamidopropylamine Oxide (Cas No: 68155-09-9), Myristamine oxide (Cas No: 3332-27-2) and Soyamidopropylamine Oxide (Cas No: 223707-70-8).

Preferred imidazoline surfactants include Disodium cocoamphodiacetate (Cas No: 68650-39-5), Disodium lauroamphodiacetate (Cas No: 14350-97-1), Sodium lauroamphoacetate (Cas No: 26837-33-2), Disodium cocoamphodipropionate (Cas No: 68604-71-7) and Sodium cocoamphoacetate (Cas No: 68334-21-4).

For the amphoteric surfactants, the charge of the hydrophilic part is controlled by the pH of the solution. This means that they can act as anionic surfactant in an alkalic solution or as cationic surfactant in an acidic solution.

Anionic Surfactants

When the hydrophilic part of the surfactant consists of a negatively charged group like alkyl sulphonate, alkyl sulphate or carboxylate or alkyl benzene sulphonates. Anionic surfactants neutralized the biocides effect of PHMB and therefor the combination of these two is not desirable. For this reason, the antimicrobial composition in this invention does not include anionic surfactants.

Humectant

The antimicrobial formula comprising at least one humectant. A dried wound cannot be healed. Humectants are used in formulations to increase the moisture content of the skin. Humectants promote water retention within the stratum corneum and prevent wounds from drying.

Humectants can be selected from a group comprising glycerine, lecithin, dipropylene glycol, polyethylene glycol and its derivate, 1,2-propylene glycol, 1,3 butylene glycol, and 1,2,6-hexanetriol, beta-sitosterol, inositol, glyceryl stearate, panthenol, and xylitol.

Solvent

The solvent may be selected from the group comprising Lactate Ringer solution, Ringer solution without lactate, Normal saline and purified water as a solvent. In the present invention purified water by distillation is preferably selected a solvent.

Buffer

The composition has preferably a pH between 4.0 and 8, in particular between 5 and 7 and preferably between 5.5 and 6.5. The role of wound bed pH is significant during the healing of wounds, and prolonged acidification of the wound bed has been shown to increase the healing rate in chronic venous leg ulcers. Suitable buffers to adjust pH can include sodium citrate, potassium citrate, and citric acid. Another preferred buffer for pH adjustment is a combination of disodium ethylenediaminetetraacetic acid salt and trisodium ethylenediaminetetraacetic acid salt.

Gelling Agent

A gelling agent, is a substance which can increase the viscosity of a liquid without substantially changing other properties. However, any cellulose derivative (e.g. methyl cellulose, hydroxypropyl methylcellulose, carboxymethylcellulose, hydroxyethyl cellulose) may be used in order to get a gel form of the composition either alone or in combination with other gelling agents. Another preferred gelling agent is carboxypolymethylene, available under the trade mark Carbopol®. Carbopol® 934P type is a high purified product and can be used in the formulation of the present invention.

In a preferred aspect, the aqueous antimicrobial compositions described herein include biocidal polymeric biguanides at a concentration ranging from 100 ppm to 10,000 ppm, or ranging from 300 ppm to 5,000 ppm, or ranging from 1,000 ppm to 2,000 ppm, or ranging from 750 ppm to 1,500 ppm, or ranging from 750 ppm to 1,250 ppm, or ranging from 850 ppm to 1,150 ppm.

When quaternary ammonium compound is present, it is preferably present in an amount in the range 50 ppm to 10,000 ppm in the diluted form, more preferably in an amount in the range 500 ppm to 5,000 ppm, more preferably in an amount in the range 1,000 to 2,000 ppm, or ranging from 750 ppm to 1,500 ppm, or ranging from 750 ppm to 1,250 ppm, or ranging from 850 ppm to 1,150 ppm The amount of metal ion chelating agents is at least 200 ppm. A preferred concentration ranging is from 300 ppm to 10,000 ppm, or ranging from 750 ppm to 5,000 ppm, or ranging from 1,000 to 3,000 ppm, or ranging from 1500 ppm to 2,500 ppm, or ranging from 1750 ppm to 2,250 ppm, or ranging from 1850 ppm to 2,150 ppm. EDTA would provide antibiofilm ability by chelating calcium and magnesium ions, which maintain the structure of the biofilm, and remove iron which is vital to microbial virulence and pathogenicity.

In a preferred aspect, the formulation is a solution comprising at least one non-ionic or at least one amphoteric surfactant or mixtures thereof at a concentration of from 100 ppm to 10,000 ppm in the diluted form, or ranging from 500 ppm to 5,000, or ranging from 2,000 ppm to 4,000 ppm, or ranging from 1500 ppm to 2,500 ppm, or ranging from 1750 ppm to 2,250 ppm, or ranging from 1850 ppm to 2,150 ppm.

The amount of humectant agent is at least 5,000 ppm. A preferred concentration ranging is from 70,000 to 100,000 ppm, or ranging from 30,000 ppm to 100,000 ppm. More preferably 40,000 ppm to 60,000 ppm or 75,000 ppm to 90,000 ppm.

The formulation for gels consists of 0.05-10% gelling agent by weight, or 0.5-5 wt %, or 1-3 wt %. or 1.5-2 wt % and completed to 100% by adding solvent.

In topical applications, the antimicrobial composition may be prepared in different forms, such as, but not limited to, liquids, creams, foams, lotions, gels and aerosols. The composition of the invention can be administered by using wound dressing materials and non-woven, foams, sponges, swabs, surgical gauze pad, cloth. The materials may be saturated or soaked in any one of the composition of the invention, as defined above.

In topical application, the antimicrobial composition product may also be administered to wounds or body cavities in liquid form for manually or instillation or automatically irrigation in conjunction with Negative Pressure Wound Therapy devices.

The liquid flow system and wound dressing utilize a Negative Pressure Wound Therapy System including a negative pressure source device and negative pressure wound dressing and connecting tubes.

The liquid flow system may draw liquid form of said composition by gravity feed system. The liquid flow system may draw liquid form of said composition by using an electrical or mechanical pump.

Figure 1:
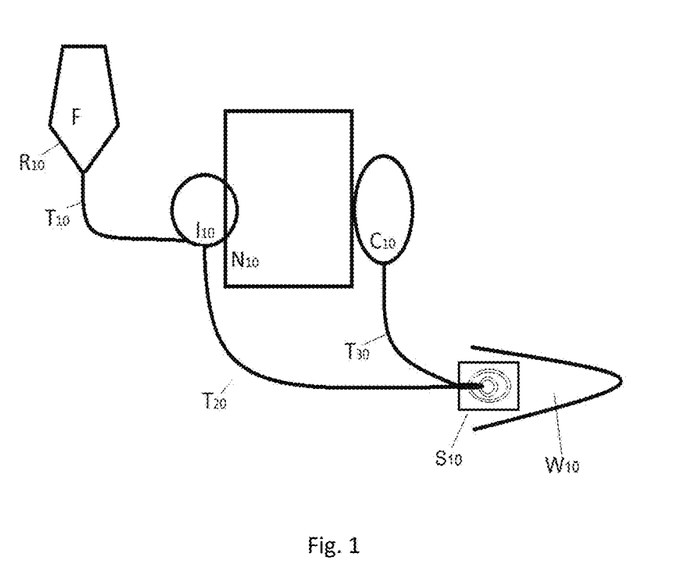
FIG. 1 shows a negative pressure system adapted for use in wound healing.

FIG. 1 shows a system or liquid flow comprising a negative pressure source N10, a canister (C10) for collecting wound exudate, a reservoir (R10) containing the composition (F) as defined above, a liquid injector device (110) for transferring a (predetermined) volume of the composition and connector tubes (T10, T20, T30) to transfer the composition to and from an infected soft tissue or bone (S10). A wound dressing (W10) may be used that can be soaked with the composition of the invention. Adhesive film or tape may be used to stabilize the wound dressing and tubes.

The system may also comprises a control unit (not shown) adapted for controlling the flow of composition to and from the wound. The control unit may be adapted to start the negative pressure source after a holding time of between 5 and 60 minutes, so that the composition is removed from the wound and fresh composition is added to the wound. The system may include valves positioned on the tubes or the reservoir, canister, etc. to further control the flow of composition through the tubes.

The system may utilize the control unit, which may be a computerize system, to "start" and "stop" to control delivery of a certain volume of the said composition to a wound dressing.

The system may after a "holding time" start the negative pressure device to draw the said composition away from the wound dressing.

Said holding time is about 5 to 60 minutes, preferably 10 to 30 minutes, and most preferably 20 minutes in order for the composition to have an antibacterial and cleansing effect.

Formulations, especially topical formulations of the antimicrobial composition may additionally comprise diluents, excipients and other additives commonly used in pharmaceutical formulations, such as for example emulsifiers, gelling agents, moisturizers, stabilizers, time release agents.

Examples on Formulation

Compositions according to the present invention include a biguanide and a chelating agent. The composition may further include other ingredients as outlined above. The following compositions have been prepared;

Example 1

| Agents | Amount (ppm) |
| --- | --- |
| 1) PHMB | 1000 |
| 2) EDTA | 2000 |
| 3) Glycerin, humectant | 50000 |
| 4) Polysorbate 60 | 1000 |
| 5) Cocobetaine | 1000 |
| 6) Purified water | To 100% |

Example 2

| Agents | Amount |
| --- | --- |
| 1) PHMB | 1000 |
| 2) EDTA | 2000 |
| 3) Glycerin | 50000 |
| 4) Polysorbate 60 | 1000 |
| 5) Undecylenamidopropylbetainesurfactants | 1000 |
| 6) Purified water | To 100% |

Example 3

| Agents | Amount (ppm) |
| --- | --- |
| 1) PHMB | 1000 |
| 2) Benzalkoniumchloride | 1000 |
| 3) EDTA | 2000 |
| 4) Glycerin | 50000 |
| 5) Polysorbate 60 | 1000 |
| 6) Cocobetaine | 1000 |
| 7) Purified water | To 100% |

Example 4

| Agents | Amount (ppm) |
| --- | --- |
| 1) PHMB | 1000 |
| 2) Benzalkonium chloride | 1000 |
| 3) EDTA | 2000 |
| 4) Glycerin | 50000 |
| 5) Polysorbate 60 | 1000 |
| 6) Undecylenamidopropyl betaine | 1000 |
| 7) Purified water | To 100% |

Example 5

| Agents | Amount (ppm) |
| --- | --- |
| 1) PHMB | 1000 |
| 2) EDTA | 2000 |
| 3) Glycerin | 85000 |
| 4) Polysorbate 60 | 1000 |
| 5) Cocobetaine | 1000 |
| 6) Hydroxyethyl cellulose | 1.8 wt. % |
| 7) Purified water | To 100% |

Example 6

| Agents | Amount (ppm) |
| --- | --- |
| 1) PHMB | 1000 |
| 2) EDTA | 2000 |
| 3) Glycerin | 50000 |
| 4) Polysorbate 60 | 1000 |
| 5) Undecylenamidopropyl betaine | 1000 |
| 6) Hydroxyethyl cellulose | 1.8 wt. % |
| 7) Purified water | To 100% |

Example 7

| Agents | Amount (ppm) |
| --- | --- |
| 1) PHMB | 1000 |
| 2) Benzalkonium chloride | 500 |
| 3) EDTA | 2000 |
| 4) Glycerin | 85000 |
| 5) Polysorbate 60 | 1000 |
| 6) Cocobetaine | 1000 |
| 7) Hydroxyethyl cellulose | 1.8 wt. % |
| 8) Purified water | To 100% |

Example 8

| Agents | Amount (ppm) |
| --- | --- |
| 1) PHMB | 1000 |
| 2) Benzalkonium chloride | 500 |
| 3) EDTA | 2000 |
| 4) Glycerin | 85000 |
| 5) Polysorbate 60 | 1000 |
| 6) Undecylenamidopropyl betaine | 1000 |
| 7) Hydroxyethyl cellulose | 1.8 wt. % |
| 8) Purified water | To 100% |

Experimental Animal Study
Experiment 1
Animals and Excisional Wound Model

This work followed the guidelines of National Institute of Health for the Care and Use of Laboratory Animals. Twenty-two healthy adult male Sprague-Dawley rats (mean weight 350 g) were selected for this experimental work. The rats were kept in clean and separate wire bottom cages, and housed in temperature-controlled (22±2° C.) and humidity-controlled (55±15%) rooms with 12-hour light:dark photo cycles. All the rats had free access to equal amounts of standard animal food and water. The rats were matched their environment for one week before starting the study.

Before wounding, the rats were anaesthetized with an intramuscular injection of thiopental sodium (40 mg/kg; Biochemie, GmbH, Austria) and xylazine (10 mg/kg; Alfasan International, Woerden, Netherlands); then, after the back hair was shaved, the site of wound creation was disinfected with alcohol ethylic solution. Next, a full-thickness excisional circular skin wound (diameter of 20 mm and depth of 2 mm) was created on the dorsum of each rat using scissors and forceps.

To conduct the research, the rats were randomly categorized into two groups (n=11): (1): the group for which the composition according to this invention (example 2) was applied on the wound surface area (group 1); and (2): the group for which Medihoney, Comvita Ltd, New Zealand, was applied on the wound surface area (group 2). During the study period, the aforementioned products were applied daily to the wounds with a disposable applicator so that a thin layer that fully covered the wound surface area was created (no dressing was used in the experiment). Both groups were followed for 21 days.

Photographic Assessment of Wound Healing

Figure 2:
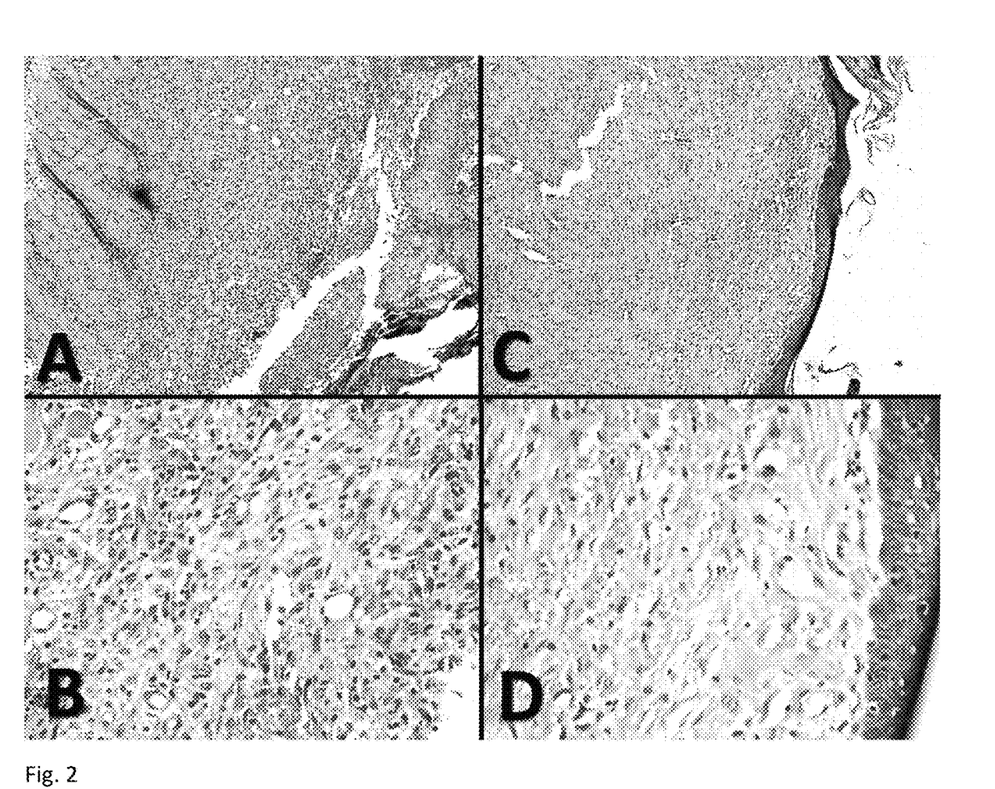
FIG. 2 shows A (X100), B (X400); Histopathologic changes in the ulcers of Group PHMB on day 7 showed ulceration, chronic inflammation, and granulation tissue formation, and C (X100), D (X400); Histopathologic changes in the lesions of the same group on day 21 showed full re-epithelialization and neovascularization.

The healing process was monitored photographically from images of each skin wound taken with a 12.1 megapixel digital camera (PowerShot G9; Canon, Tokyo, Japan). To calibrate the magnification of the photographs, the camera was kept at a fixed distance of 10 cm from the wound surface (in a vertical view), and a fine-line ruler was placed at wound level at the time of imaging. Photos were taken on days 0, 7, and 21 post-wounding and analyzed using the Photoshop CS Program (Adobe Systems, San Jose, Calif., USA) (analysis menu; record measurements command). The results are shown in FIG. 2.

Histopathological Evaluation of Wound Healing

Semi-circular full-thickness skin biopsies from the wound sites of rats in both groups were taken on days 7 (half of the wound site with a margin of 2 mm) and 21 (the remaining part with a 2 mm margin) post-wounding. The animals were anesthetized by inhalation of ether on day 7 and euthanized with ether on day 21.

Tissue samples were washed with sterile normal saline, immediately fixed in buffered formaldehyde (10% formalin), and sent for histopathological assessment using established techniques (haematoxylin and eosin and Masson-trichrome stainings, and light microscopic examination).

The scoring system developed by Abramov and his colleagues for histopathological evaluation of the wound healing process was adapted to this study. This scoring system uses the following features: the amount of acute and chronic inflammatory infiltrates, the amount and maturation of granulation tissue, neovascularization, collagen deposition, and reepithelialisation. All the investigators who assessed the tissue samples or analysed the images were blinded to the agents given.

Statistical Analysis

The results are presented as mean±standard deviation (SD). Statistical comparisons were made using the Mann-Whitney U-test (SPSS Statistics software, version 16; Chicago, Ill., USA). P values less than 0.05 were considered statistically significant.

Results
Wound Contraction

The mean±SD values of wound surface area were calculated for each of the groups using the images taken on days 0, 7, and 21, post-wounding (Table 1). According to the results, there was no statistically significant difference in the mean wound surface area between the two groups in the 0, 7th, and 21st days of experiment. The rats' wounds showed no apparent sign of infection during the study period.

TABLE 1

The mean ± SD of wound surface area (mm²) in two groups on different days post-wounding.

| Day | 0 | 7 | 21 |
|---|---|---|---|
| Group 1 | 310.16 ± 13.22 | 48.54 ± 11.34 | 0.0 ± 0.00 |
| Group 2 | 316.87 ± 13.67 | 50.83 ± 9.49 | 0.26 ± 0.49 |
| P-value | 0.123 | 0.234 | 0.187 |

Histopathological Examinations

The results of the histopathological assessment are summarized in Table 2. According to this study, there was no statistically significant difference between the two groups regarding the factors of acute and chronic inflammation, amount and maturation of granulation tissue, neovascularization, collagen deposition, and reepithelialisation. No necrosis was seen.

CONCLUSION

It has been shown that, daily topical application of the composition according to the present invention (example 2), on fresh skin wounds has similar efficacy to Medical honey for the healing process.

In addition, no significant negative impact (i.e. cellular toxicity) on the parameters that were involved in the wound healing process occurred following the usage of the composition of the present invention (example 2).

TABLE 2

Mean ± SD values of histopathological scores of wound healing among the different study groups.

| | Day 7 | | | Day 21 | | |
|---|---|---|---|---|---|---|
| Parameter | Group 1 | Group 2 | P-Value | Group 1 | Group 2 | P-Value |
| Acute and Chronic inflammation | 2.00 ± 0.89 | 1.90 ± 0.94 | 1.00 | 2.54 ± 0.52 | 1.81 ± 0.87 | .069 |
| Amount of granulation tissue | 2.54 ± 0.52 | 2.63 ± 0.50 | 0.60 | 0.72 ± 1.00 | 0.81 ± 0.75 | 0.34 |
| Granulation tissue maturation | 2.45 ± 0.52 | 2.54 ± 0.52 | 0.91 | 1.36 ± 1.56 | 2.09 ± 1.37 | 0.28 |
| Collagen deposition | 1.63 ± 0.67 | 2.00 ± 0.44 | 0.08 | 1.54 ± 0.52 | 2.00 ± 0.89 | 0.23 |
| Reepithelialization | 0.45 ± 1.03 | 0.54 ± 1.03 | 0.51 | 2.72 ± 0.64 | 2.72 ± 0.64 | 0.83 |
| Neovascularization | 3.00 ± 0.00 | 3.00 ± 0.00 | 1.00 | 3.00 ± 0.00 | 3.00 ± 0.00 | 1.00 |

The invention claimed is:

1. An antimicrobial and cleansing composition comprising:
   polyhexamethylene biguanide (ppm),
   EDTA (ppm), and
   a solvent (wt %),
   wherein the ratio of the polyhexamethylene biguanide to the EDTA is between 0.75:2.25 and 1:2.

2. The composition according to claim 1, wherein the composition further comprises:
   a quaternaryammonium salt (ppm),
   wherein the ratio of the polyhexamethylene biguanide to the EDTA to the quaternary ammonium salt is between 0.75:2.25:0.30 and 1:2:1.

3. The composition according to claim 1, wherein the composition further comprises:
   at least one surfactant (ppm), and
   wherein the ratio of the polyhexamethylene biguanide to the EDTA to the at least one surfactant is between 0.75:2.25:0.75 and 1:2:2.

4. The composition according to claim 1, wherein the composition further comprises:
   a quaternaryammonium salt (ppm),
   at least one surfactant (ppm), and
   wherein the ratio of the polyhexamethylene biguanide to EDTA to the quaternaryammonium salt to the at least one surfactant is between 0.75:2.25:0.30:0.75 and 1:2:1:2.

5. The composition according to claim 1, which further comprises of a humectant.

6. The composition according to claim 1, wherein the composition comprises:
   the polyhexamethylene biguanide in an amount of 750 to 1250 ppm, or about 1000 ppm,
   the EDTA in an amount of 1750 to 2250 ppm, or about 2000 ppm, and
   the solvent up to 100 wt %,
   and one or more of the following ingredients:
   a quaternary ammonium salt in an amount of 400 to 1250 ppm, or about 500 or 1000 ppm,
   at least one surfactant in an amount of 1750 to 2250 ppm, or about 2000 ppm,
   a humectant in an amount of 40000 to 100000 ppm, or about 50000 or 85000 ppm, and
   a gelling agent in an amount of 1.5 to 2.5 wt %, or about 1.8 wt %.

7. The composition according to claim 6, wherein the composition consists of
   polyhexamethylene biguanide in an amount of 750 to 1250 ppm, or about 1000 ppm,
   EDTA in an amount of 1750 to 2250 ppm, or about 2000 ppm,
   polysorbate 60 in an amount of 750 to 1250 ppm, or about 1000 ppm,
   undecylenamidopropyl betaine in an amount of 750 to 1250 ppm, or about 1000 ppm,
   water up to 100 wt %, and
   glycerin in an amount of 40000 to 100000 ppm, or about 50000 or 85000 ppm.

8. The composition according to claim 6, wherein the composition consists of
   polyhexamethylene biguanide in an amount of 750 to 1250 ppm, or about 1000 ppm,
   EDTA in an amount of 1750 to 2250 ppm, or about 2000 ppm,
   benzalkonium chloride in an amount of 750 to 1250 ppm, or about 1000 ppm,
   polysorbate 60 in an amount of 750 to 1250 ppm, or about 1000 ppm,
   undecylenamidopropyl betaine in an amount of 750 to 1250 ppm, or about 1000 ppm,
   water up to 100 wt %, and
   glycerin in an amount of 40000 to 100000 ppm, or about 50000 or 85000 ppm.

9. The composition according to claim 1, wherein composition is a liquid at a pH from 5 to 7.

10. The composition according to claim 3, wherein the at least one surfactant includes at least one non-ionic surfactant or at least one amphoteric surfactant or mixtures thereof, which surfactants have a hydrophilic-lipophilic balance value between 8 and 20, or between 10 and 18.

11. A method of treatment or reduction of a disease, disorder or condition in a subject selected from the group consisting of acute or chronic infection, acute or chronic inflammation, diabetic ulcers, second-degree partial-thickness burns, traumatic wounds, *Acanthamoeba keratitis*, necrotizing fasciitis, venous stasis disease, pressure ulcerations, and carcinomas, comprising administering a therapeutic effective amount of a composition according to claim 1 to the subject.

12. The method of claim 11, wherein the disease, disorder, or condition is a diabetic ulcer, second-degree partial-thickness burn, traumatic wound, or pressure ulceration.

13. The method of claim 11 wherein the disease, disorder or condition is acute or chronic infected wounds, or acute or chronic inflamed wounds.

14. A liquid flow system housing the composition according to claim 1, whereby the system comprises a negative pressure source, a canister for collecting wound exudate, a reservoir containing the composition, a liquid injector device for transferring a predetermined volume of the composition and connector tubes to transfer the composition to and from an infected soft tissue or bone, a negative pressure wound dressing, which system is adapted to draw fluid from the reservoir to the wound dressing and draw fluid away from the wound dressing after a holding time of 5 to 60 minutes.

15. The composition according to claim 1, wherein the composition further comprises one or more of the following ingredients:
   a quaternary ammonium salt,
   at least one surfactant,
   a humectant, and/or
   a gelling agent.

16. The composition according to claim 1, wherein the composition has minimal or no cellular toxicity for mammal cells.

\* \* \* \* \*